United States Patent [19]

Mullins et al.

[11] Patent Number: 5,167,946

[45] Date of Patent: Dec. 1, 1992

[54] DIARYL CARBONATE PROCESS

[75] Inventors: Michael J. Mullins; Rafael Galvan; Thomas A. Chamberlin, all of Midland, Mich.

[73] Assignee: The Dow Chemical Company, Midland, Mich.

[21] Appl. No.: 784,141

[22] Filed: Oct. 29, 1991

Related U.S. Application Data

[63] Continuation of Ser. No. 634,622, Dec. 27, 1990, abandoned.

[51] Int. Cl.⁵ .............................................. C01B 7/00
[52] U.S. Cl. ................................. 423/481; 558/274
[58] Field of Search ..................... 423/481; 558/274

[56] References Cited

U.S. PATENT DOCUMENTS

| | | | |
|---|---|---|---|
| 2,362,865 | 11/1944 | Tryon et al. | 558/274 |
| 2,837,555 | 6/1958 | Lee | 558/274 |
| 3,251,873 | 5/1966 | Kurkjy et al. | 558/274 |
| 4,012,406 | 3/1977 | Buysch et al. | 558/274 |
| 4,045,464 | 8/1977 | Romano et al. | 558/274 |

FOREIGN PATENT DOCUMENTS 61-151140  7/1986  Japan ............................ 423/481

OTHER PUBLICATIONS

Chemical Abstract: 84(17): 121495h, 1976.

Primary Examiner—John Niebling
Assistant Examiner—Brian M. Bolam

[57] ABSTRACT

Diaryl carbonates are prepared by the catalyzed reaction of an aryl hydroxide with a carbonyl halide in the liquid phase at a temperature from greater than 100° to less than 150° C.

8 Claims, 2 Drawing Sheets

CONVERSION TIME AS A FUNCTION OF TEMPERATURE

PHENOL CONVERSION VERSUS TIME

DIARYL CARBONATE PROCESS

CROSS-REFERENCE TO RELATED APPLICATION

This is a continuation of application Ser. No. 634,622 filed Dec. 27, 1990, now abandoned.

The present invention relates to a process for the production of diaryl carbonates, and more particularly to a process for the liquid phase reaction of aromatic hydroxy compounds with carbonyl halides for the production of high purity diaryl carbonates with the elimination of anhydrous hydrogen halide.

BACKGROUND OF THE INVENTION

Diaryl carbonates are useful as starting materials for the preparation of polycarbonates by melt processes. This melt process typically is conducted at temperatures up to 320° C. in order to drive off aryl hydroxy compound and increase the molecular weight to useful levels. Small amounts (1-10 ppm) of basic ester exchange catalysts, such as alkali metal hydroxides, are commonly employed. An important advantage of this melt process over the solution process is that the polymer product melt may be directly extruded and chopped into pellets for sale. Isolation and purification from viscous solutions is not necessary, nor is the handling and recycling of large volumes of solvent.

U.S. Pat. No. 2,362,865 discloses the reaction of phenol and phosgene to form diphenyl carbonate. The reaction employed amphoteric metal catalysts and reaction temperatures from 150° to 250° C., preferably 180° to 250° C. The reaction is conducted in the melt without a solvent, i.e. under neat conditions. U.S. Pat. No. 3,251,873 discloses a similar process utilizing non-amphoteric metal catalysts and an organic solvent. Suitable reaction temperatures are from 50° to 250° C. depending on the reflux temperatures of the organic solvent at atmospheric pressure. U.S. Pat. No. 2,837,555 discloses ammonium halide catalysts, neat reaction conditions and reactor temperatures from 150° to 250° C. for a process similar to that of U.S. Pat. No. 3,251,873. U.S. Pat. No. 4,012,406 discloses the reaction of phenols and phosgene using heterocyclic basic nitrogen catalysts and temperatures from 25° to 200° C. in a gaseous reaction medium.

SUMMARY OF THE INVENTION

The invention of this application is a process for the production of a diaryl carbonate and hydrogen halide comprising contacting an aromatic hydroxy compound with a carbonyl halide in the presence of a catalyst under liquid phase reaction conditions at a reaction temperature of greater than 100° and less than 150° C. Preferred reaction temperatures are 110° to 145° C., most preferably 125° to 135° C.

DETAILED DESCRIPTION

It has been found advantageous for the process of this invention to be carried out in the specified temperature range both in terms of production rate and in ease of operation. At high temperatures, i.e. greater than 150° C., the phenolic reactants are volatilized from the reaction mixture and tend to solidify in the condensor employed for recycle of carbonyl halide. Thus the use of lower temperatures reduces the severity of this problem. Most surprisingly, however, it has been found that the temperature range of the process of the instant invention achieves an enhanced diphenyl carbonate production rate compared to the use of lower or higher temperatures. This result is entirely unexpected based on knowledge of the prior art.

Figure 1:
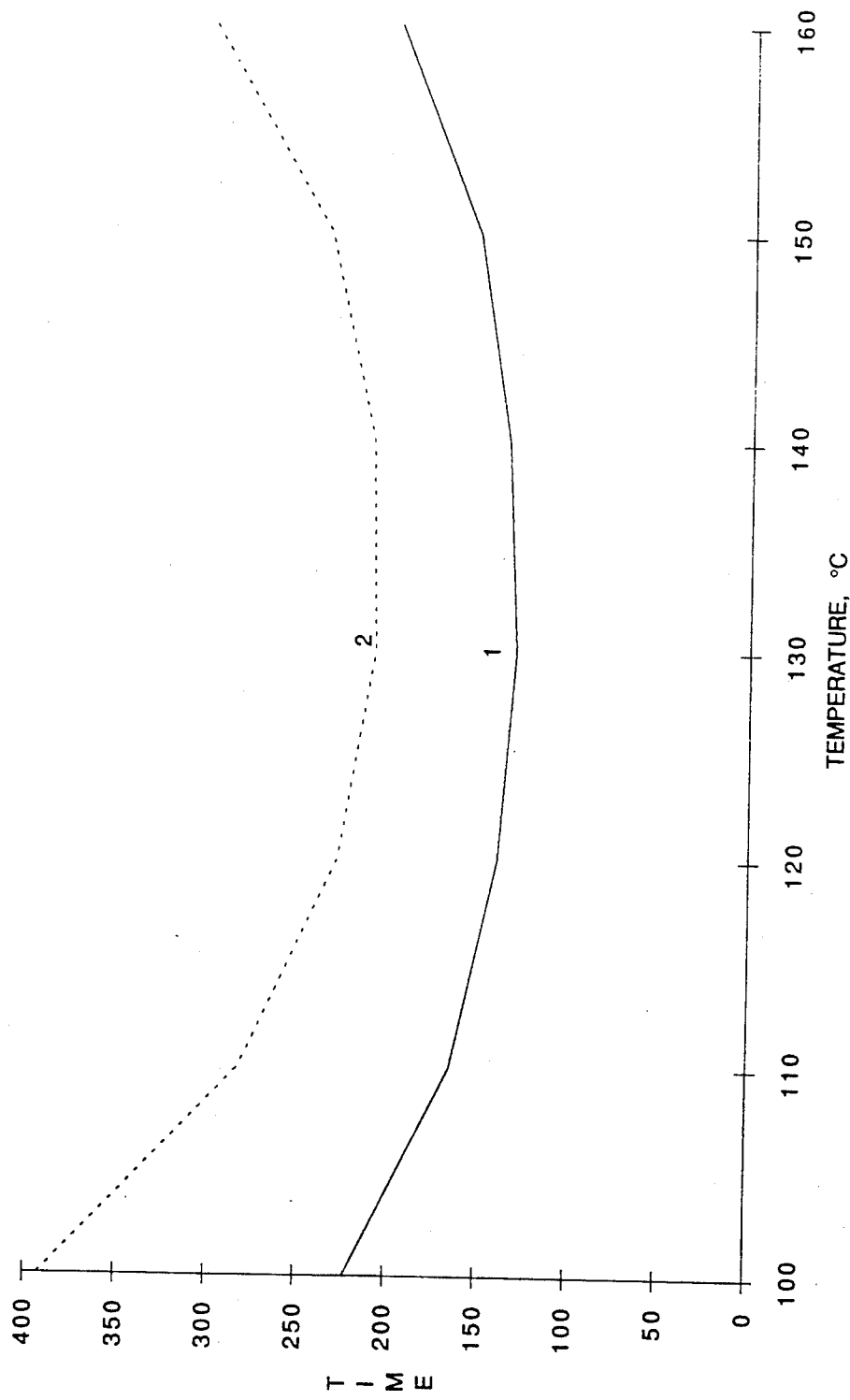
FIG. 1 depicts calculated times to reach phenol conversions of 50 and 75 percent at various temperatures.
Figure 2:
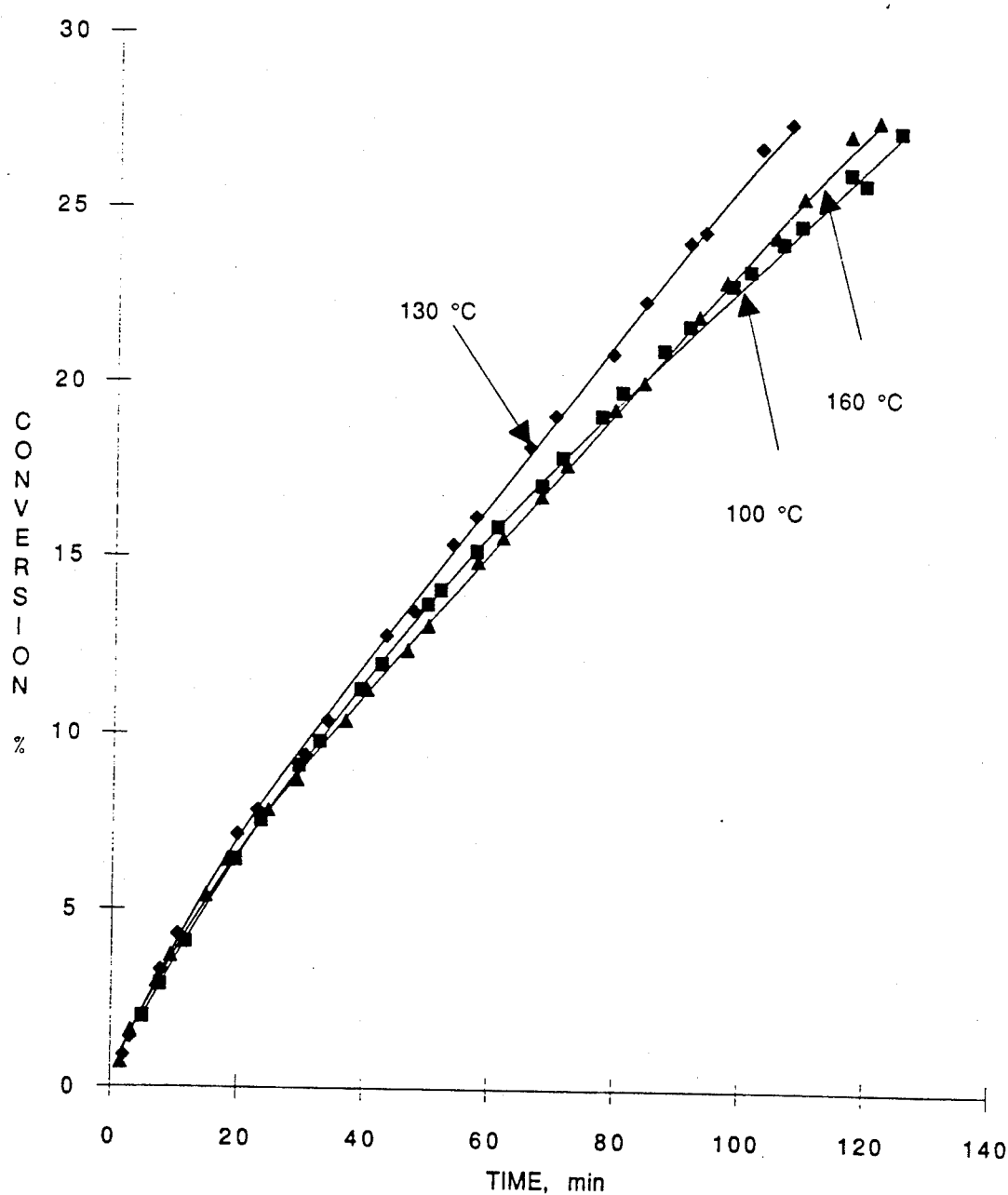
FIG. 2 depicts actual conversions of phenol after stated times for temperatures of 100°, 130° and 160° C.

This result is illustrated in FIG. 1 which is a graphic representation of time required to reach phenol conversions of 50 percent (1) and 75 percent (2) at various temperatures as predicted from a model derived from data generated by Example 2. Actual conversions of phenol at three temperatures are shown in FIG. 2.

Suitable aromatic hydroxy starting materials for the present process are represented by the general formula:

where Ar is an aryl or substituted aryl group containing 6 to 16 carbon atoms, R independently selected each occurrence is alkyl, aryl, alkenyl, aryloxy, or alkoxy of 1-12 carbon atoms, and n is an integer. Preferred aromatic hydroxy starting materials are represented by the formula:

where R independently each occurrence is alkyl, aryl, alkenyl, aryloxy, or alkoxy of 1-12 carbon atoms, and n is an integer of 0-5. More highly preferred are compounds of formula II wherein R independently each occurrence is alkyl, aryl, alkenyl, aryloxy, or alkoxy

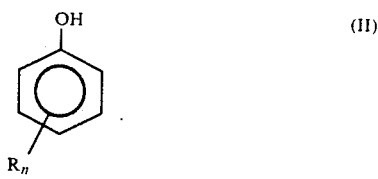

of 1-6 carbon atoms and n is an integer of 0-3. A most preferred aromatic hydroxy compound is phenol.

A preferred carbonyl halide starting reactant is phosgene.

In a preferred embodiment the aromatic monohydroxy compound is phenol, the carbonyl halide is phosgene and the products of the reaction are diphenyl carbonate (DPC) and anhydrous hydrogen chloride.

Suitable catalysts are those previously disclosed in the art. Preferred catalysts for the process of the present invention comprise aluminum containing materials, including aluminum salts, organoaluminum compounds and aluminum metal. Preferred aluminum containing materials include aluminum halides, aryloxides, alkoxides, arylalkoxides, arylhalides, alkylhalides, sulfides, carbides and carbonates. A most preferred catalyst is aluminum trichloride.

A catalytic amount of the catalyst may be dissolved or dispersed or supported in the reaction medium. In one embodiment of the present invention the catalyst is simply dispersed in the reaction medium. If the reaction medium includes a noninteracting solvent it is desirable that the catalyst dissolve in the solvent.

The concentration of catalyst which provides a catalytic amount of the catalyst in the reaction system of the process of the present invention preferably ranges from 0.001 to 10 mole percent based on the number of moles of the aromatic hydroxy compound. A highly preferred range for the concentration of the catalyst is from 0.05 to 1 mole percent, with the most preferred range being from 0.1 mole percent to 0.5 mole percent.

The mole ratio of the reactants are not critical to success. However, a preferred ratio of carbonyl halide to aromatic hydroxy compound is from 1:1 to 1:3, most preferably 1:1.5 to 1:2.5.

The hydrogen chloride produced in the reaction can be removed continuously or intermittently, as desired, and as necessary to relieve the pressure build-up due to the production of this gaseous product.

The process of the present invention desirably is carried out neat, that is, under conditions in which a melt of the aromatic hydroxy compound serves as the reaction medium for the reaction. Accordingly a melt is established. A catalytic amount of the catalyst is added to the melt and dispersed. The carbonyl halide is then introduced to the reaction mixture preferably under conditions to promote gas/liquid contact, e.g. by using a stirred reactor or bubble column reactors, etc. The hydrogen halide gas coproduct is allowed to exit from the reactor through a gas condensor, which traps carbonyl halide and returns it to the reactor. Carbonyl halide is added until preferably at least about 80 percent conversion of the aromatic hydroxy compound is achieved, and the crude material is then distilled preferably under vacuum to remove aromatic hydroxy compound and optionally diaryl carbonate. The residues remaining after distillation contain residual active catalyst which may be reused.

In a preferred embodiment the process is conducted as a continuous process. The carbonyl halide is added continuously to the reaction medium, which is continuously supplemented by the addition of aromatic hydroxy compound. The reaction product is drained off continuously and distilled to separate the diaryl carbonate product from unreacted aromatic hydroxy compound and catalyst, both of which may be recycled.

In another embodiment the process of the present invention desirably is carried out in an inert reaction medium which comprises an inert atmosphere, preferably nitrogen. The reaction may be run with or without a noninteracting liquid diluent. Suitable diluents include aromatic hydrocarbons, which may be halogenated, of from 6 to 16 carbon atoms. Examples include xylene, toluene, ethylbenzene, cumene, diisopropylbenzene, chlorobenzene and dichlorobenzene. Other desirable diluents include aliphatic halogenated hydrocarbons such as trichloroethylene, methylene chloride and tetrachloroethylene. A preferred diluent is dichlorobenzene. A mixture of two or more diluents may be used.

Operation within the above indicated temperature limitations has numerous advantages for the process of the present invention in addition to the inherent economic advantage due to energy savings when compared to operating at elevated temperatures.

To illustrate further the advantages of the present invention, a reaction of phenol and phosgene is illustrated.

The normal boiling point of phosgene is 6° C. In order to prevent the escape of this hazardous material and to use it efficiently, condensor means normally cooled to a temperature below 6° C. are employed. In a typical prior art process run at 170° C. or higher, the vapor pressure of phenol is high, approximately 0.7 atm. A condensor operating at a temperature of 6° C. would be quickly blocked with phenol which freezes at 41° C. There is then a danger of explosion due to a buildup of the hydrogen chloride generated in the reaction of the process. Any pathway provided for the escape of hydrogen chloride would be similarly plugged by phenol. To avoid such events, a second condensing means to remove the phenol from the gas stream before the phosgene is condensed must be used. This adds considerable expense to the process design.

However, in the process of the present invention, which is carried out at lower temperatures, the vapor pressure of phenol is much less, for example, about 0.054 atm at 100° C. Phosgene can be condensed and returned to the reaction medium by a single condensor means. The problem of phenol freezing and condensor fouling has been found to be insignificant.

Surprisingly, it has also been found that rates of reaction for the process of the present invention carried out in the temperature ranges discussed above, with all other factors being equal, are better than the rates of reaction observed in processes conducted at higher or lower temperatures.

The reasons for the improved performance at the specified temperature range in a liquid reaction medium are believed to be as follows: The reaction between phenol and a carbonyl halide is temperature dependent. The rate of this reaction increases with increasing temperature. However, it has now been discovered that the solubility of carbonyl halide in aromatic hydroxide or other liquid reaction medium drops dramatically as temperature increases. Moreover in an open system, i.e. one in which total gaseous components are controlled by a condensor or similar means, the partial pressure of phosgene in the reactor diminishes rapidly as the boiling point of the aromatic hydroxy compound is approached, i.e. temperature greater than 150° C. The combined effect of the last two principles operates to limit the rate of mass transfer of phosgene into the liquid phase. Thus, the observed rate of phenol conversion in a liquid phase system is a function of both the rate of reaction and the rate of phosgene mass transfer and reaches an optimum at a temperature in the range previously specified.

The following example is provided to illustrate the process of the present invention, and is not intended to limit the scope of the present invention in any way.

EXAMPLE 1

A 2-liter 4-necked Morton flask (indented sides), equipped with a dry-ice condensor on top of a Vigreux column, mechanical stirring, a gas inlet, and an internal thermometer was used. The flask was also equipped with a sampling port, which consisted of a side-arm normally closed with a Teflon stopcock and sealed with a septum. The flask was heated with a heating mantle, and the temperature was measured using a thermocouple inserted to the bottom of a glass well immersed under the liquid level.

The flask was charged with molten phenol (1007.93 g), and the catalyst (10.30 g AlCl$_3$) was carefully added. After the solution temperature had equilibrated at 100° C., phosgene was delivered from a 1-liter holding cylinder placed on a balance accurate to 0.1 g. This gas stream was mixed with 0.1 mL/min N$_2$ to prevent oxygen intrusion and to reduce the possibility of the reaction solution backing up into the gas delivery system. After entering the reaction flask through the gas inlet (no sparge tube was used), the gases exited through Vigreux column and past the dry ice condenser, and finally into a scrubber column. A rate of about 1.5 g/min (0.91 moles/hour) of phosgene was maintained throughout the reaction. After 307 min a total of 498.5 g of phosgene had been added. A 50 uL aliquot was removed at this point, and GC analysis revealed an 82 percent conversion of phenol. Phosgene was added for 34 more minutes until 551.0 g total had been added. Further phosgene addition was stopped. Heating at 100° C. was continued for an additional 30 minutes to reduce the concentration of phenyl chloroformate below detectable limits. The crude product was distilled using water aspirator vacuum with a short path still on top of a 30 cm Vigreux column. The first fraction (bp 88°–170° C., 122.12 g) was a mixture of recovered phenol (68 wt. percent) and diphenyl carbonate (32 wt. percent). A higher boiling fraction (bp 175°–178° C., 934.43 g) consisted of diphenyl carbonate and 0.47 wt. percent phenol. The pot residue (85.16 g) consisted of undistilled diphenyl carbonate and catalyst residue.

EXAMPLE 2

The reaction kinetics and mass transfer rates for the process at different temperatures were determined in a 1 L, 4-necked flask equipped with a gas inlet for nitrogen and phosgene, an internal thermocouple, mechanical stirring (semicircular polytetrafluoroethylene paddle), a dry-ice condensor, and a caustic scrubber to neutralize the exit gases.

The flask was charged with phenol, an internal standard for gas chromatographic analysis (diphenyl methane), and anhydrous aluminum chloride (0.20 mole percent based in phenol). The yellow slurry was heated to the desired temperature and phosgene was introduced at an appropriate rate to maximize conversion without waste of phosgene. The catalyst eventually completely dissolved to form a red-orange solution within about 80 minutes after the phosgene addition was started. Samples (50 uL) were removed at 3–4 minute intervals, dissolved in 2 mL toluene and analyzed by gas chromatography.

Results, expressed as time (minutes) to reach 50, line 1 and 75, line 2 percent conversion of phenol at 100°, 110°, 120°, 130°, 140°, 150° and 160° C. were simulated based on a model derived from the above rate and reaction kinetics data. Results are contained in FIG. 1. As may be seen, the time to produce a given conversion of phenol is observed to reach a minimum for temperatures between 100° and 150° C., preferably 110° and 140° C.

Actual conversions at 100°, 130° and 160° C. versus time are provided in FIG. 2. It is seen that operation at 130° C. achieves improved performance compared to operation at either 100° or 160° C. thereby substantiating the surprising result that maximum effeciency is achieved at temperatures in the region between 100° and 150° C.

What is claimed is:

1. A process for the production of a diaryl carbonate and hydrogen halide comprising contacting an aromatic hydroxy compound with a carbonyl halide in the presence of an aluminum catalyst under liquid phase reaction conditions at a reaction temperature of greater than 100° and less than 150° C.

2. The process of claim 1 wherein the reaction temperature is from 110° C. to about 145° C.

3. The process of claim 2 wherein the reaction temperature is from about 125° C. to about 135° C.

4. The process of claim 1 wherein the aromatic hydroxy compound is phenol and the carbonyl halide is phosgene.

5. The process of claim 1 wherein the catalyst is aluminum trichloride.

6. The process of claim 1 wherein the reaction is conducted neat in a melt of the aromatic hydroxy compound.

7. The process of claim 1 wherein the ratio of carbonyl halide to aromatic hydroxy compound is 1:1 to 1:3.

8. The process of claim 1 wherein the catalyst is present in an amount from 0.001 to 10 mole percent based on aromatic hydroxy compound.

* * * * *